(12) United States Patent
Demos et al.

(10) Patent No.: US 8,190,242 B2
(45) Date of Patent: May 29, 2012

(54) PORTABLE LASER SYNTHESIZER FOR HIGH-SPEED MULTI-DIMENSIONAL SPECTROSCOPY

(75) Inventors: Stavros G. Demos, Livermore, CA (US); Miroslav Y. Shverdin, Sunnyvale, CA (US); Michael D. Shirk, Brentwood, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 385 days.

(21) Appl. No.: 12/507,585

(22) Filed: Jul. 22, 2009

(65) Prior Publication Data

US 2010/0020319 A1    Jan. 28, 2010

Related U.S. Application Data

(63) Continuation-in-part of application No. 11/031,936, filed on Jan. 8, 2005, now Pat. No. 7,587,236.

(60) Provisional application No. 61/082,582, filed on Jul. 22, 2008.

(51) Int. Cl.
*A61B 6/00* (2006.01)
*G02F 1/35* (2006.01)

(52) U.S. Cl. .......................... 600/473; 600/476; 359/327
(58) Field of Classification Search .................. 600/473, 600/476; 359/326, 327
See application file for complete search history.

(56) References Cited

U.S. PATENT DOCUMENTS

| | | | | |
|---|---|---|---|---|
| 4,379,409 A | * | 4/1983 | Primbsch et al. | 73/643 |
| 6,825,928 B2 | * | 11/2004 | Liu et al. | 356/317 |
| 6,958,854 B1 | * | 10/2005 | Merriam | 359/327 |

* cited by examiner

*Primary Examiner* — Michael Rozanski
(74) *Attorney, Agent, or Firm* — John P. Wooldridge

(57) ABSTRACT

Portable, field-deployable laser synthesizer devices designed for multi-dimensional spectrometry and time-resolved and/or hyperspectral imaging include a coherent light source which simultaneously produces a very broad, energetic, discrete spectrum spanning through or within the ultraviolet, visible, and near infrared wavelengths. The light output is spectrally resolved and each wavelength is delayed with respect to each other. A probe enables light delivery to a target. For multidimensional spectroscopy applications, the probe can collect the resulting emission and deliver this radiation to a time gated spectrometer for temporal and spectral analysis.

21 Claims, 3 Drawing Sheets

PORTABLE LASER SYNTHESIZER FOR HIGH-SPEED MULTI-DIMENSIONAL SPECTROSCOPY

This application claims priority to U.S. Provisional Application No. 61/082,582, titled: "Portable Laser Synthesizer for High-Speed Multi-Dimensional Spectroscopy," filed Jul. 22, 2008.

This is a continuation-in-part of U.S. patent application Ser. No. 11/031,936, now U.S. Pat. No. 7,587,236, titled: "Spectroscopy for the Detection of Ischemic Tissue Injury," filed Jan. 8, 2005, incorporated herein by reference.

The United States Government has rights in this invention pursuant to Contract No. DE-AC52-07NA27344 between the United States Department of Energy and Lawrence Livermore National Security, LLC.

BACKGROUND OF THE INVENTION

1. Field of the Invention

The present invention relates to the spectral response of matter to applied light, and more specifically, it relates to spectroscopic tissue characterization and imaging.

2. Description of Related Art

Detection and imaging of living tissue is a major objective in a variety of fields from biology and biophysics to biomedicine and clinical studies, enabling discovery of cellular function, screening for diseases, synthesis of new drugs and evaluation of treatment plans. Because of the microscopic size among the various cellular constituents, techniques such as confocal reflectance and confocal fluorescence spectroscopy are used, e.g., to measure the response of matter to applied light. Such response may include fluorescence, scattering, absorption and Raman scattering. In vivo imaging is particularly important because it enables real time feedback, and could greatly reduce the duration of exploratory or therapeutic procedures, and allows rapid optimization of design and treatment parameters.

There is a tremendous medical, technological and scientific need for a portable apparatus for rapid spectroscopic characterization and imaging of materials including tissues. Though a great deal of progress has occurred, the potential of this technology has not been fully explored due to various technological limitations including insufficient computer power, availability and cost of fast electronics and availability of suitable light sources. However, it is anticipated that continuous technological advances could address existing limitations in the near future. Generally, the response of tissue to the applied light occurs on a nanosecond timescale and is highly wavelength dependent. The presence of many different tissue types renders the response function very complicated. The ability to identify and map out tissue components or tissue constituents would be greatly enhanced if it were possible to simultaneously record the temporal and spectral response to exposure to light pulses at different wavelengths that are temporally short compared to the response of the tissue.

Currently, methods for spectroscopic analysis in real time (suitable for in-vivo applications) are performed either in the spectral domain, using a CW laser at a particular wavelength or in the time domain using a short (most often picosecond) pulse at a single wavelength. Tunable laser sources are limited in their bandwidth. Currently, pulsed laser radiation at multiple wavelengths is possible by either utilizing many distinct lasers simultaneously, which is prohibitively expensive and the availability of laser wavelengths is very limited and does not lead to portability, or by utilizing nonlinear conversion techniques, namely optical parametric oscillators. The second technique requires a long time (as long as 10s of seconds) to tune from one frequency to the next. This prevents in vivo analysis, since the time necessary to acquire data is prohibitively long. It is apparent that the field of spectroscopic characterization and imaging of material and tissues would greatly benefit by the availability of a laser source capable of simultaneously producing light (or laser) pulses at discrete wavelengths across a wide bandwidth.

Recently, several techniques efficiently producing wide bandwidth sources have been experimentally demonstrated. These techniques rely on the interaction of intense laser beams with a gas. Raman scattering occurs when a laser beam at frequency $\omega_L$ excites a rotational or a vibrational molecular transition, at frequency $\omega_R$. The molecular motion modulates the applied laser beam and produces new sidebands at the sum and difference frequencies, ($\omega_L-\omega_R$, $\omega_L+\omega_R$, $\omega_L-2\omega_R$, $\omega_L+2\omega_R$, etc.). This process is typically inefficient and generates few sidebands. The Raman generation processes becomes highly efficient when two intense laser beams with an appropriately chosen frequency difference approximately equal to the Raman transition are applied simultaneously and collinearly. This produces a set of discrete frequencies that span over four octaves of bandwidths (from 200 nm to 3 µm). The pulse duration at each sideband is equal or shorter to that of the excitation laser pulses and can be in the range of $10^{-15}$ to $10^{-8}$ seconds. The sidebands are generated collinearly in a nearly $TEM_{00}$ mode and are both spatially and temporally coherent.

SUMMARY OF THE INVENTION

It is an object of the present invention to utilize the coherent Raman modulation technique to construct a portable light source producing laser pulses at discrete wavelengths across a wide bandwidth.

Another object is to integrate a portable light source into a system for spectral and temporal characterization of materials including tissues.

It is another object to integrate a portable light source into a system for hyperspectral imaging.

Still another object is to integrate a portable light source into a time resolved imaging system for capturing multiple images of the evolution at pre-determined time points of a single event with exposure time equal to the temporal duration of each individual pulse.

These and other objects will be apparent based on the disclosure herein.

Embodiments of the present invention provide and utilize portable, field-deployable devices, each sometimes generically herein termed "Laser Synthesizer," designed for multi-dimensional spectrometry and time-resolved and/or hyper-spectral imaging. Embodiments include a coherent light source which simultaneously produces a very broad, energetic, discrete spectrum spanning through or within the ultraviolet, visible, and/or near infrared wavelengths. The light output can be spectrally resolved and each wavelength can be fiber-optically coupled and the generated wavelengths can be delayed with respect to each other, e.g., by varying the lengths of the individual fibers. The fibers can be bundled together into a probe, enabling light delivery to a target. For multidimensional spectroscopy applications, the probe can collect the resulting emission and deliver this radiation to a time gated spectrometer for temporal and spectral analysis. Complete spectroscopic characterization, consisting of excitation radiation, emission radiation, spectrally resolved emission lifetimes, and signal intensity can be recorded in a fraction of a second, allowing real time data acquisition and processing. For imaging applications, one or more CCD cameras can record images under illumination at different wavelengths to obtain a multispectral or hyperspectral image of the object. The entire data acquisition can occur in a fraction of a second. Embodiments provide unprecedented capabilities in microscopy, spectroscopy, hyperspectral imaging and, time-resolved imaging with applications for remote sensing in adverse environments, sequential acquisitions of images of single events with high or ultrafast temporal resolution and frame rate, biology, and biomedicine. Capabilities of embodiments of the invention are based on a coherent Raman modulation technique, where two laser fields at appropriate intensities and frequencies efficiently excite a Raman transition in a low pressure gas. The resulting molecular motion modulates the input laser fields to efficiently generate spectral sidebands separated by the frequency of the Raman transition. Other uses of embodiments of the invention include disease detection (e.g., cancer detection), remote sensing, tissue imaging and analysis.

The present invention will benefit a wide range of biomedical, clinical, and remote sensing applications and will greatly upgrade and extend the capabilities of spectroscopy, microscopy and hyperspectral and time resolved imaging and could enable novel medical procedures, scientific studies, and security measures. U.S. Provisional Application No. 61/082,582, titled: "Portable Laser Synthesizer for High-Speed Multi-Dimensional Spectroscopy," filed Jul. 22, 2008, is incorporated herein by reference.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1A:
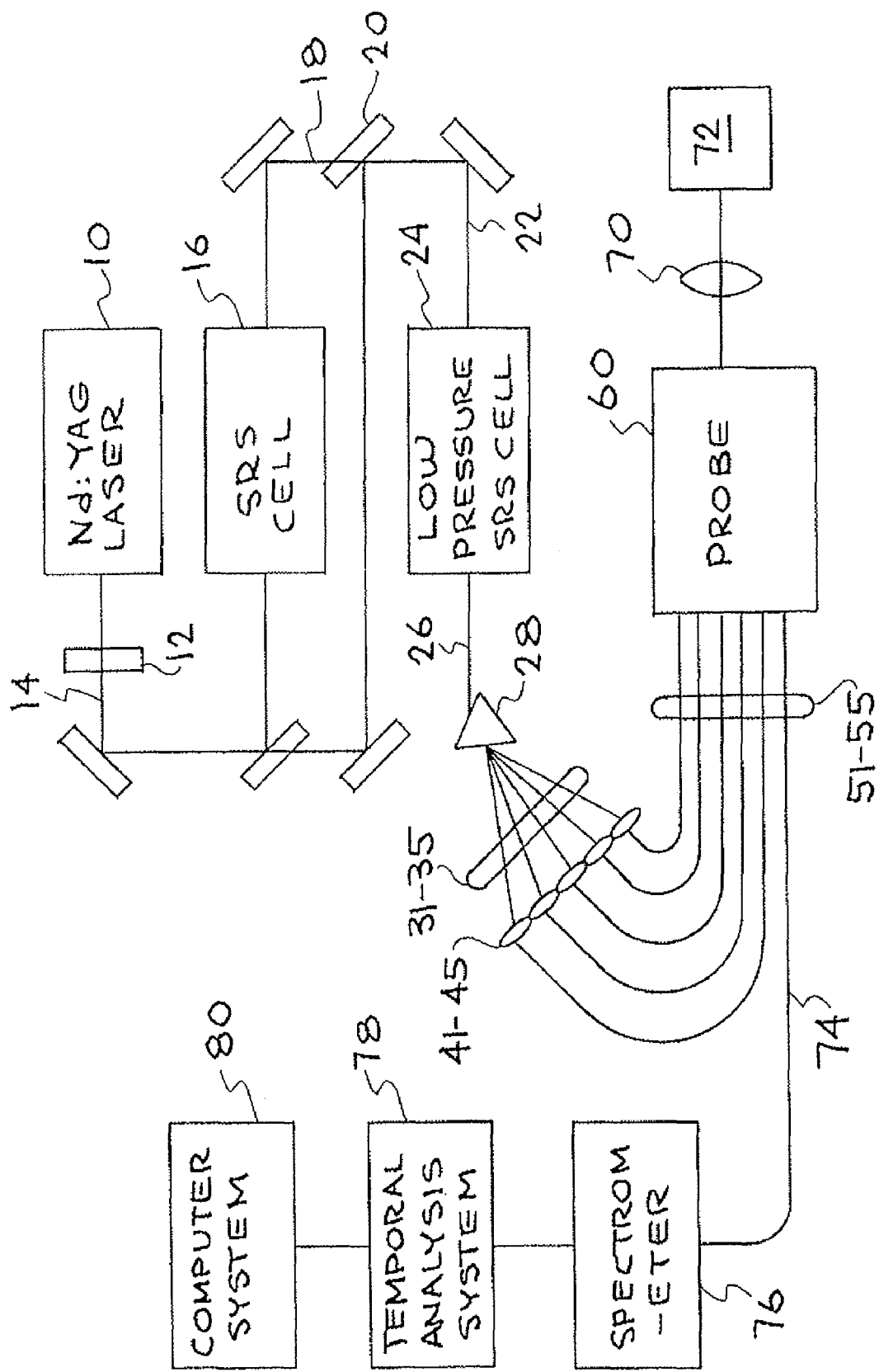
FIG. 1A shows an exemplary embodiment of a portable optical synthesizer configuration according to principles of the present invention.
Figure 1B:
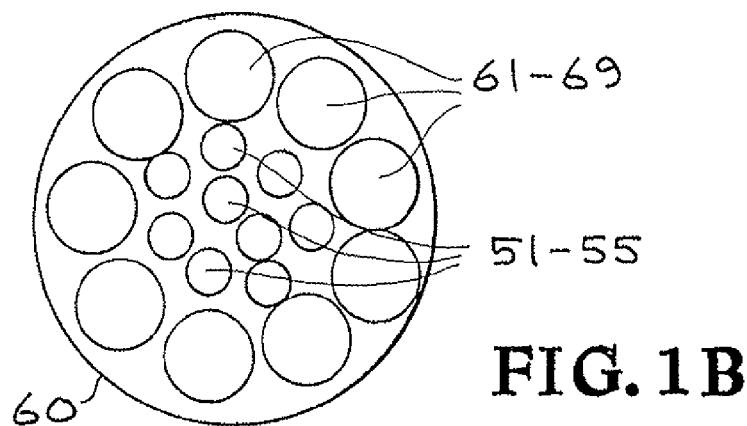
FIG. 1B shows the output face of the probe of FIG. 1A.

FIG. 1A illustrates an exemplary embodiment of the present invention. An Nd:YAG laser 10, having an operating wavelength of 1.06 μm, is frequency tripled with a configuration of non-linear crystals 12 to produce a beam 14 of laser light having a wavelength of 355 nm. Part of beam 14 interacts with stimulated Raman scattering (SRS) cell 16 to produce a first SRS output beam 18. Another part of beam 14 is combined with output beam 18 at dichroic optic 20 to produce a combined beam 22. Dichroic optic 20 is coated to allow transmission of the wavelength of the output beam 18 and reflection the wavelength of beam 14. Combined beam 22 interacts with SRS cell 24 to produce a second SRS cell output beam 26. A prism 28 spectrally separates the wavelengths of beam 26. FIG. 2 shows a demonstrated output spectra dispersed by prism 28. A portion of the output spectra is indicated by reference numbers 31-35 in FIG. 1A, which are focused by lenses 4145 into fiber optics 51-55. Each of fiber optics 51-55 is a different length and terminates in a probe 60. The output face of probe 60 is shown in FIG. 1B and includes the output faces of fiber optics 51-55 and larger diameter collection fibers 61-69. The output light propagating from the output face of probe 60 is directed by lens 70 onto a target 72. Lens 70 collects a portion of the light produced by interaction of the output light with target 72 and is routed by fiber bundle 74 to a spectrometer 76, which is operatively connected to a temporal analysis system 78 and a computer system 80. The embodiment of FIG. 1A is but one example of the present invention. A method and apparatus for Raman Stokes and anti-Stokes scattering is described in U.S. Pat. No. 6,958,854, incorporated herein by reference. The following describes general and specific requirements to accomplish the principles of the present invention.

A basic requirement of the present invention is the provision of a coherent light source which simultaneously produces a very broad, energetic, discrete spectrum spanning ultraviolet, visible, and near infrared spectral regions, as represented in FIG. 1A as the second SRS cell output beam 26. The generated wavelengths are delayed with respect to each other by varying the lengths of the individual fibers. The fibers are bundled together into a probe, which delivers light to a target. For multidimensional spectroscopy applications, the probe collects the resulting emission and delivers this radiation to a suitable system for temporal and spectral analysis. The resulting data is processed and analyzed in real-time to yield a multi-dimensional spectroscopic characterization of the target. The complete system can be compact, portable, and cost effective such that it is suitable for field deployment. The present invention can be used as the probe system described in U.S. patent application Ser. No. 11/031,936, titled: "Spectroscopy for the Detection of Ischemic Tissue Injury," filed Jan. 8, 2005, incorporated herein by reference.

In the embodiment of FIG. 1A, and similar configurations, stimulated Raman scattering (SRS) from the interaction of a portion of the pump laser beam with a gas in a first SRS cell produces a Stokes field which is then combined at a dichroic mirror with a remaining portion of the pump laser beam. This combined beam is then sent to a second (low pressure) SRS cell to produce a comb of sidebands. Note that other means for producing a comb of sidebands are within the scope of the invention, examples of which are provided infra. Based on the present disclosure, still other sideband production techniques will be apparent to those skilled in the art, and are within the scope of this invention. In some embodiments, both SRS cells contain the same gas and the pump laser is configured to produce a transform limited nanosecond pulse with at least 100 mJ of energy. The gas in each cell is set at an appropriate pressure. Each cell is cooled with liquid nitrogen to reduce Raman linewidth and increase Raman gain.

The induced delay between sidebands can be made variable, e.g., on the order of 10s of nanoseconds, which is slightly longer than the emission lifetimes of tissues. Other techniques for dispersion and delay are within the scope of the invention, examples of which are provided infra. Based on the present disclosure, still other dispersion and delay techniques will be apparent to those skilled in the art, and are within the scope of this invention. The emission spectrum produced by the interaction of the delayed sidebands with a target is then gathered by the collection fibers in the probe and delivered to a time-gated spectrometer for spectral and temporal analysis. The data matrix consists of the excitation spectra (for specific emission wavelengths and spectral bands), the spectrum of the emission radiation (for all excitation wavelengths), the spectrally resolved emission lifetimes (for all or selected excitation wavelengths), decay time constants (or fitting parameters to a temporal profile) of each signal component and the signal intensity (normalized via a suitable method) of each of the previous signal components. The probe can be coupled through a catheter or an endoscopic probe to facilitate noninvasive scanning and mapping of interior or exterior tissue locations or organs.

Because the light source simultaneously generates all of the sidebands, data can be readily available to the operator (limited by the data processing and transfer rate of the detection system). The information can then be deconvolved and analyzed to identify biochemical and tissue structure information that can be related to tissue status, onset or progression of disease or response to treatment. This rapid rate of data acquisition enables utilization of the optical synthesizer for in vivo procedures and experiments.

Figure 2A:
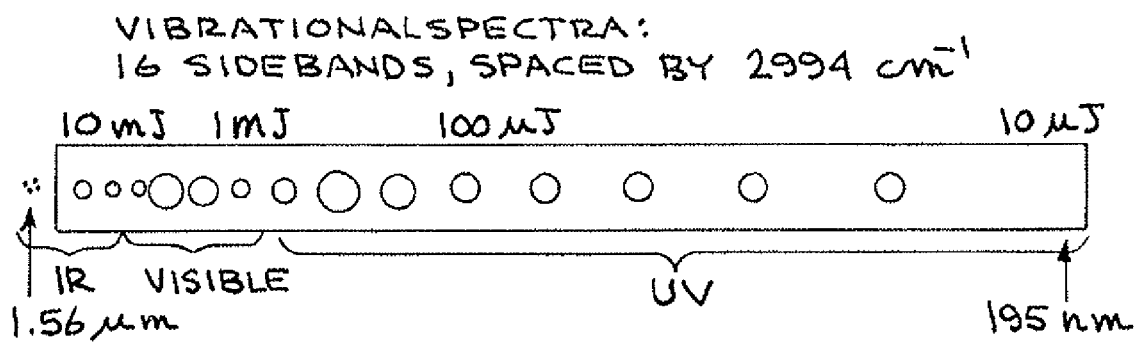
FIG. 2A shows an image of the Raman sidebands (vibrational spectra) after spatially separated spanning from 195 nm to 1560 nm, spaced by about 3000 $cm^{-1}$ (90 THz).
Figure 2B:
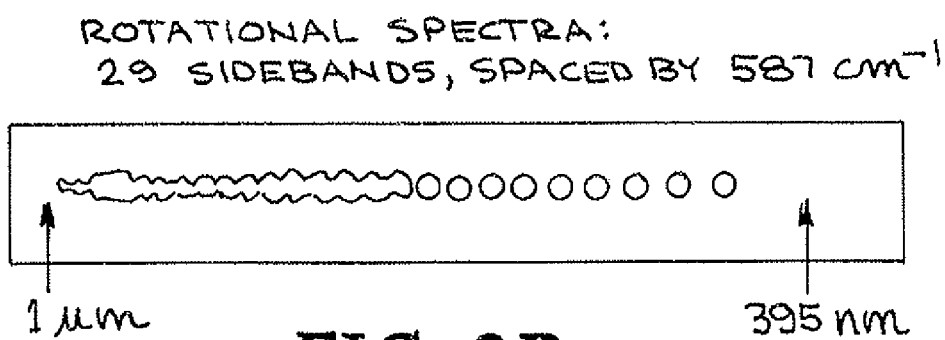
FIG. 2B shows the rotational spectra, spanning from 395 nm to 1000 nm, spaced by about 590 $cm^{-1}$.
Figure 3A:
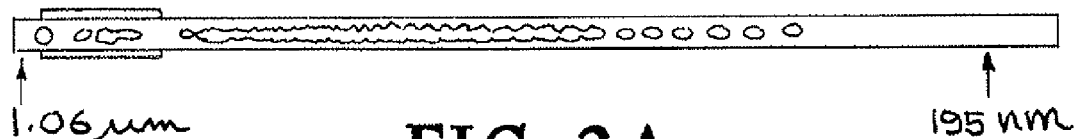
FIG. 3A shows the multiplicative spectra.
Figure 3B:
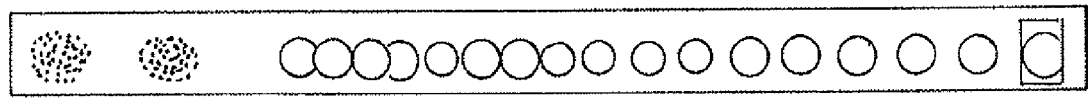
FIG. 3B shows a magnification of the box covering the visible spectrum of FIG. 3A.
Figure 3C:
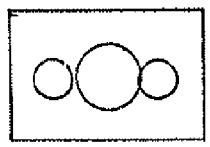
FIG. 3C shows a magnification of the box at the far right of FIG. 3B.

FIG. 2A shows an image of the Raman sidebands (vibrational spectra) after spatially separated spanning from 195 nm to 1560 nm, spaced in energy by about 3000 $cm^{-1}$ (90 THz). The sidebands of FIG. 2A were produced by using deuterium in the SRS cells. FIG. 2B shows the rotational spectra, spanning from 395 nm to 1000 nm, spaced in energy by about 590 $cm^{-1}$. FIG. 3A shows the multiplicative spectra. The box covering the visible spectrum of FIG. 3A is expanded in FIG. 3B. The box at the far right of FIG. 3B is expanded in FIG. 3C.

In another method for producing a wide comb of sidebands for time and frequency resolved analysis, an ultrashort pulse can be focused into a photonic bandgap fiber for supercontinuum generation—a continuous spectral band from visible to near infrared. Discrete bands can be separated out by, for example, dispersing the colors with gratings and prisms and then coupling individual bands into fibers.

Another method for producing a wide comb of sidebands is known as impulsive Raman scattering. This method consists of exciting a gas medium with an ultrashort (sub picosecond) intense laser pulse, called a pump pulse. A weak ultrashort (10-50 femtosecond) probe pulse is then delayed with respect to the pump pulse and sent into the excited gas medium. The probe pulse interacts with the Raman excited states and produces Stokes and anti-Stokes sidebands. Experiments have shown generation of discrete colors from visible to near infrared.

In another embodiment, a laser synthesizer according to the present invention is coupled to a microscope system to characterize and map out tissue based on the spectral and temporal characteristics of the recorded signal at each pixel corresponding to discrete locations within the tissue sample arising from cellular or sub-cellular components, yielding biochemical and cellular structure information. This can be utilized, e.g., to identify boundaries between healthy and cancerous or abnormal tissue to minimize invasiveness and/or effectiveness of a surgical procedure.

In another application, an embodiment of the present laser synthesizer is used to identify precursors of diseases to enable early detection and treatment. In drug studies, the laser synthesizer can be used to monitor in real time the distribution and effects of the drug delivered to cell cultures or experimental animals.

Another application combines an embodiment of the present laser synthesizer with fluorescence markers, such as nanoparticles, fluorescing contrast agents or quantum dots to study cellular processes. Each protein of interest can be tagged with a different marker having unique combination of spectral and temporal characteristics and the temporal and spectral fluorescence response of each marker can be recorded to resolve the presence and distribution of the various proteins, their microenvironment and particular processes (e.g. protein folding). A similar tagging technique can be utilized to study other molecular processes.

In another application, an embodiment is utilized for hyperspectral imaging. Different wavelengths illuminate the target and one or more CCD cameras then record the resulting spectrally resolved images of the reflected light from the target. Hyperspectral imaging is currently used to identify items such as military camouflage, hazardous waste emissions, counterfeit items, mineral samples, vegetation etc. Similarly, hyperspectral images capturing the spectral response of the emission from a target can be acquired. For example, the images resulting from emission in a specific part of the spectrum can be acquired for a sequence of excitation wavelengths or the image of a sequence of different emission wavelengths under excitation at a specific wavelength, or a combination of the above. One can further add the temporal response of the emission for a 5- or 6-dimensional mapping of the target region including the spatial location (2 or 3-dimensions), the excitation, the emission and the emission lifetime.

In another application, an embodiment is utilized for time resolved imaging with ultrafast shutter speed and frame rate. Different wavelengths illuminate the target and a single lens system is used to capture the image of the target location. The image formed is spectrally analyzed and the different image components (from each individual wavelength) are recorded separately. Since the arrival of each wavelength at the target location is different, the images captured at each wavelength represent the state of the target region at different time points. This method can be used for the acquisition of a large number of images with ultrafast temporal resolution during the timeline of single events evolving in time scales that can be as short as on the order of $10^{-12}$ seconds or shorter. Such instrumentation does not currently exist.

Spectroscopic images of the target can be captured using various image acquisition methods. Spectral imaging typically refers to acquisition of a single image that contains some type of spectroscopic information. An example is an emission image captured over the entire emission spectral band under excitation at a single wavelength. Multi-spectral imaging is an extension of spectral imaging with the acquisition of multiple images of the target that contain different spectroscopic information. An example is a number of emission images over distinct emission spectral bands under excitation at a single wavelength. Hyper-spectral imaging is an extension of multi-spectral imaging with the acquisition of multiple images of the target to form an image stack that contains detailed spectroscopic information. An example is acquiring the emission image at spectral steps of every 5 nm through the entire spectral region of the emission under excitation at a single wavelength. This image stack can be used to retrieve the spectrum at any single location within the imaged area of the target.

Images can be captured using the various target properties, including the reflection spectral characteristics, the absorption spectral characteristics, the emission spectral characteristics, the excitation spectral characteristics and the index of refraction spectral characteristics.

Images can be captured in a number of geometries, including transmission geometry (TR), also called shadowgraphic imaging or shadowgraphy, where the light propagates through the target and the image is captured along the direction of propagation. The image is formed by the photons that were not absorbed or reflected or refracted during the interaction of the illumination with the target. Backscattering Geometry (BS) which includes all other configurations except the TR geometry but most commonly, the image is formed at approximately the opposite direction for the direction of illumination (photons captured undergo about 180 degrees change in direction of propagation during the interaction with the target). The image is formed by the photons that were reflected or emitted by the target.

Images can be captured using different imaging modes. Light scattering imaging is realized by recording an intensity map of the target when illuminated at a single wavelength. Using one or more illumination wavelengths, it can be implemented using the spectral, multispectral or hyperspectral image acquisition methods. Emission or Fluorescence imaging is realized by recording an intensity map of the emission of the target over a specific spectral range when illuminated at a single excitation wavelength. Using one or more emission wavelengths, it can be implemented using the spectral, multispectral or hyperspectral image acquisition methods. Excitation imaging is realized by recording an intensity map of the emission of the target over a specific spectral range when illuminated at a single excitation wavelength. Using one or more excitation wavelengths, it can be implemented using the spectral, multispectral or hyperspectral image acquisition methods. Using different emission spectral bands, multiple sets of multispectral or hyperspectral excitation images of the target can be acquired. Polarization sensitive imaging can be utilized in the light scattering, emission, or excitation imaging modes by using polarized illumination and recording one or both the orthogonal polarization image components of the recorded signal (reflection or emission). Fluorescence lifetime imaging typically refers to acquisition of images that depicts the emission lifetime of the target under excitation at a single wavelength. Fluorescence lifetime imaging can be combined with spectral, multispectral or hyperspectral imaging to capture the spectral dependence of the emission (either as a function of the excitation wavelength, the emission wavelength or in combination) lifetime image. Multimodal imaging refers to the utilization of various modes of image acquisition. In time resolved imaging, images of a single event are captured at different time points. It is used to capture the evolution of single and unique events. It can be combined with spectral or multispectral (it is practically impossible for hyperspectral) imaging to capture the spectral dependence of the observed event within the target region.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A method, comprising:
    producing spatially separated pulses of light, wherein each pulse of said pulses comprises a unique wavelength spectral segment relative to each other said pulse;
    delivering said pulses to tissue, wherein said pulses are delivered to said tissue in a time series, wherein after a first pulse is delivered to said tissue, each consecutive pulse is delivered to said tissue within about 10 ns of its preceding pulse and wherein said time series is delivered to said tissue within about 10 μs, wherein said wavelength of each pulse delivered to said tissue interacts with said tissue to generate produced light;
    collecting said produced light to produce data; and
    temporally and spectrally analyzing said data.

2. The method of claim 1, wherein said spatially separated pulses of light are produced from a light source having a very broad, energetic, discrete spectrum.

3. The method of claim 1, wherein said spatially separated pulses of light are produced from a light source having a spectrum spanning from ultraviolet to near infrared wavelengths.

4. The method of claim 1, wherein said spatially separated pulses of light are produced from a coherent beam based on a coherent Raman modulation technique, wherein two laser fields excite a Raman transition in a low pressure gas, wherein the resulting molecular motion modulates the input laser fields to efficiently generate spectral sidebands separated by the frequency of the Raman transition.

5. The method of claim 4, wherein said coherent Raman modulation technique uses two cells each containing the same gas, wherein a pump laser is configured to produce a transform limited pulse and wherein each cell is cooled with liquid nitrogen to reduce Raman linewidth and increase Raman gain.

6. The method of claim 1, wherein said spatially separated pulses of light are produced by focusing an ultrashort pulse into a photonic bandgap fiber for supercontinuum generation—a continuous spectral band from visible to near infrared.

7. The method of claim 1, wherein said spatially separated pulses of light are produced by impulsive Raman scattering comprising:
    exciting a gas medium with an ultrashort (sub picosecond) intense laser pulse, called a pump pulse; and
    sending an ultrashort (10-50 femtosecond) probe pulse into said gas medium at a time delayed with respect to said pump pulse, wherein said probe pulse interacts with Raman excited states produced by said pump pulse such that said probe pulse produces Stokes and anti-Stokes sidebands.

8. The method of claim 1, wherein the step of delivering said pulses comprises optically coupling each said unique wavelength spectral segment into a fiber optic, wherein each said unique wavelength spectral segment is coupled into a separate fiber optic from that of each other said unique wavelength spectral segment, wherein each said separate fiber optic has a unique length relative to each other said separate fiber optic.

9. The method of claim 8, wherein each said unique length provides a relative delay between the transmission time through each said separate fiber optic relative to each other said separate fiber optic, wherein each said relative delay is longer than an emission lifetime of light from said tissue.

10. The method of claim 9, wherein the step of delivering said pulses comprises positioning a lens to direct output light from each said separate fiber optic to said tissue and wherein the step of collecting said produced light comprises using said lens to direct light from said tissue to collection fiber optics, wherein said collection fiber optics are optically connected to a spectrometer which is operatively connected to a temporal analysis system and a computer system.

11. The method of claim 8, further comprising forming a bundle that includes each said separate fiber optic to provide illumination from about the same location.

12. The method of claim 11, wherein said bundle is coupled through a catheter or an endoscopic probe configured for noninvasive scanning and/or mapping of interior or exterior tissue locations or organs.

13. The method of claim 1, wherein said data is selected from the group consisting of spatially separated wavelengths, emission radiation from said tissue, spectrally resolved emission lifetimes of said emission radiation from said tissue, temporal profile of said emission radiation, and signal intensity of each of the previous components.

14. The method of claim 1, wherein the step of analyzing said data comprises delivering said data to a time gated spectrometer for temporal and spectral analysis.

15. The method of claim 1, wherein the step of analyzing said data comprises analyzing images from said tissue.

16. The method of claim 15, wherein said images are spectroscopic images captured with an image acquisition method selected from the group consisting of spectral imaging, multi-spectral imaging and hyper-spectral imaging.

17. The method of claim 15, wherein said images comprise a tissue property selected from the group consisting of reflection spectral characteristics, absorption spectral characteristics, emission spectral characteristics, excitation spectral characteristics and index of refraction spectral characteristics.

18. The method of claim 15, wherein said images are captured using a geometry selected from the group consisting of a transmission geometry and a backscattering geometry.

19. The method of claim 15, wherein said images are captured using an imaging mode selected from the group consisting of a light scattering imaging, emission or fluorescence imaging, excitation imaging, polarization sensitive imaging, fluorescence lifetime imaging, multimodal imaging and time resolved imaging.

20. An apparatus, comprising:
means for producing spatially separated pulses of light, wherein each pulse of said pulses comprises a unique wavelength spectral segment relative to each other said pulse;
means for delivering said pulses to tissue, wherein said pulses are delivered to said tissue in a time series, wherein after a first pulse is delivered to said tissue, each consecutive pulse is delivered to said tissue within about 10 ns of its preceding pulse and wherein said time series is delivered to said tissue within about 10 µs, wherein said wavelength of each pulse delivered to said tissue interacts with said tissue to generate produced light;
means for collecting said produced light to produce data; and
means for temporally and spectrally analyzing said data.

21. The apparatus of claim 20, wherein said means for delivering said pulses comprises optically coupling each said unique wavelength spectral segment into an optical delay system comprising refractive and reflective elements, wherein each said wavelength spectral segment travels different optical lengths before exiting said optical delay system.

* * * * *